(12) United States Patent
Ishii et al.

(10) Patent No.: US 7,304,184 B2
(45) Date of Patent: Dec. 4, 2007

(54) PROCESS FOR PRODUCING ALLYL-CONTAINING COMPOUNDS

(75) Inventors: Yasutaka Ishii, Takatsuki (JP); Takahiro Iwahama, Himeji (JP); Tatsuya Nakano, Himeji (JP)

(73) Assignee: Daicel Chemical Industries, Ltd., Sakai-Shi (JP)

( * ) Notice: Subject to any disclaimer, the term of this patent is extended or adjusted under 35 U.S.C. 154(b) by 0 days.

(21) Appl. No.: 10/786,104

(22) Filed: Feb. 26, 2004

(65) Prior Publication Data

US 2004/0171885 A1 Sep. 2, 2004

(30) Foreign Application Priority Data

Feb. 28, 2003 (JP) ............................. 2003-052383

(51) Int. Cl.
*C07C 41/00* (2006.01)
*C07C 319/00* (2006.01)
(52) U.S. Cl. ........................................ 568/59; 568/697
(58) Field of Classification Search ................ 568/630, 568/657
See application file for complete search history.

(56) References Cited

U.S. PATENT DOCUMENTS 5,578,740 A * 11/1996 Au et al. ..................... 549/525

FOREIGN PATENT DOCUMENTS

| GB | 1 200 730 | | 7/1970 |
|---|---|---|---|
| JP | 48-43329 | | 12/1973 |
| JP | 10-511721 A | | 11/1998 |
| JP | 2004-107337 A | | 4/2004 |
| JP | 2006-501209 A | | 1/2006 |
| WO | WO96/20232 A1 | | 7/1996 |
| WO | WO 96/20232 A1 | | 7/1996 |
| WO | 2004013076 | * | 2/2004 |
| WO | WO 2004/013076 A1 | | 2/2004 |

OTHER PUBLICATIONS

Hawley's Condensed Chemical Dictionary, 13th ed., 1997.*
"Catalysis" in Kirk-Othmer Encyclopedia of Chemical Technology Copyright © 2001 by John Wiley & Sons, Inc. pp. 200-254.*
Courses in Experimental Chemistry, 4th Ed., vol. 20, p. 188-193, Jun. 5, 1992, edited by The Chemical society of Japan, Maruzen Co., Ltd.
R. Nahrwald et al., Tetrahedron, 56(38), pp. 7463-7468 (Sep. 15, 2000).
H. Kim et al., Organic Letters, 4(24), pp. 4369-4371 (2002), XP002282719.
H. Dvorakova et al., Tetrahedron Letters, 36(35), pp. 6351-6354 (1995) XP004027386.
N. Iranpoor et al., Tetrahedron, 50(24), pp. 7299-7306 (1994) XP002282720.
A.V. Malkov et al., J. Org. Chem., 64(8), 2737-2750 (1999), XP002282721.
R. Takeuchi et al., J. Am. Chem. Soc., 120(34), pp. 8647-8655 (1998), XP002282723.
R. Takeuchi et al., Organic Letters, 1(2), pp. 265-267 (1999) XP002282722.
Database CAPLUS 'Online!' Chemical Abstracts Service, Columbus, Ohio, U.S., K. Takahashi et al., "Ester exchange of carboxylic acid ester", XP002282724, retrieved from STN, Database accession No. 1974:425103, abstract, & JP 480 433 29B B4 (Torray Industries, Inc. (Dec. 18, 1973).
Database CAPLUS 'Online!' Chemical Abstracts Service, Columbus, Ohio, US; K. Takahashi et al., "Palladium-catalyzed exchange of allylic groups of ethers and esters with active hydrogen compounds. II" XP02282725, retrieved from STN, Database accession No. 1972, 98670, abstract. & Bulletin of the Chemical Society of Japan, 45(1), 230-6 CODEN: BCSJAB; ISSN: 0009-2673, 1972.
R. Mahrwald et al., Tetrahedron, 56(38), pp. 7463-7468 (Sep. 15, 2000).

(Continued)

*Primary Examiner*—Karl Puttlitz
(74) *Attorney, Agent, or Firm*—Birch, Stewart, Kolasch & Birch, LLP

(57) ABSTRACT

An allyl-containing compound represented by following Formula (3):

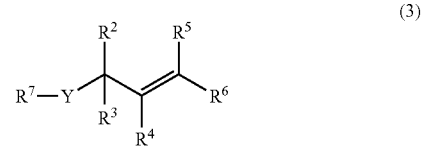

(3)

wherein $R^2$, $R^3$, $R^4$, $R^5$ and $R^6$ may be the same as or different from one another and each represent hydrogen atom or an organic group; $R^7$ represents an organic group; and Y represents oxygen atom or sulfur atom, is produced by reacting an allyl ester compound represented by following Formula (1):

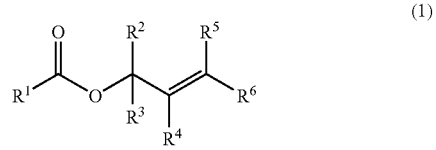

(1)

wherein $R^1$ represents hydrogen atom or an organic group; and $R^2$, $R^3$, $R^4$, $R^5$ and $R^6$ are as defined above, with a compound represented by following Formula (2):

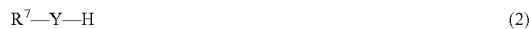

(2)

wherein $R^7$ is an organic group; and Y is as defined above, in the presence of at least one transition element compound.

5 Claims, No Drawings

OTHER PUBLICATIONS

H. Kim et al., Organic Letters, 4(24), pp. 4369-4371 (2002), XP002282719.
H. Dvorakova et al., Tetrahedron Letters, 36(35), pp. 6351-6354 (1995) XP004027388.
N. Iranpoor et al., Tetrahedron, 50(24), pp. 7299-7306 (1994) XP002282720.
A.V. Malkov et al., J. Org. Chem., 64(8), 2737-2750 (1999), XP002282721.
R. Takeuchi et al., J. Am. Chem. Soc., 120(34), pp. 8647-8655 (1998), XP002282723.
R. Takeuchi et al., Organic Letters, 1(2), pp. 265-267 (1999) XP002282722.

DATABASE CAPLUS 'Online!' Chemical Abstracts Service, Columbus, Ohio, U.S., K. Takahashi et al., "Ester exchange of carboxylic acid ester", XP002282724, retrieved from STN, Database accession No. 1974: 425103, abstract, & JP 480 433 29B B4 Toray Industries, Inc. (Dec. 18, 1973).
DATABASE CAPLUS 'Online!' Chemical Abstracts Service, Columbus, Ohio, US; K. Takahashi et al., "Palladium-catalyzed exchange of allylic groups of ethers and esters with active hydrogen compounds. II" XP002282725, retrieved from STN, Database accession No. 1972: 98670, abstract, & Bullentin of the Chemical Society of Japan, 45 (1) , 230-6 CODEN: BC8JA8; ISSN: 0009-2673, 1972.

* cited by examiner

PROCESS FOR PRODUCING ALLYL-CONTAINING COMPOUNDS

This Nonprovisional application claims priority under 35 U.S.C. § 119(a) on Patent Application No(s). 2003-052383 filed in JAPAN on Feb. 28, 2003, the entire contents of which are hereby incorporated by reference.

BACKGROUND OF THE INVENTION

1. Field of the Invention

The present invention relates to a process for producing an allyl-containing compound. Such allyl-containing compounds are useful, for example, as perfumes and intermediates in organic synthesis.

2. Description of the Related Art

Compounds containing an allyloxy group or allylthio group (hereinafter referred to as "allyl-containing compound"), such as allyl ethers, allyl thioethers, allyl esters and allyl thioesters, are useful as perfumes and intermediates in organic synthesis. For example, terpenic allyl-containing compounds have been widely used as perfumes.

Such allyl ethers are prepared, for example, by a process of replacing the halogen of an allyl halide with an alkoxide (Courses in Experimental Chemistry, 4th Ed., Vol. 20, p. 188–193, Jun. 5, 1992, edited by The Chemical Society of Japan, Maruzen Co., Ltd.). However, this process uses an equivalent amount of a base as the raw material, leading to a basic reaction system. Compounds having a complicated structure for use as perfumes may often be decomposed in such a basic reaction system. In addition, the process requires an aftertreatment for halogen-containing waste in a large amount which is formed by elimination of the halogen.

SUMMARY OF THE INVENTION

Accordingly, an object of the present invention is to provide a process for easily producing an allyl-containing compound by a catalytic reaction using a transition element compound under mild conditions.

Another object of the present invention is to provide a highly versatile process for producing an allyl-containing compound.

After intensive investigations to achieve the above objects, the present inventors have found that an allyl-containing compound can be easily prepared under mild conditions by reacting a corresponding allyl ester compound with an alcohol, thiol, carboxylic acid or thiocarboxylic acid in the presence of a specific catalyst. The present invention has been accomplished based on these findings.

The present invention provides a process for producing an allyl-containing compound represented by following Formula (3):

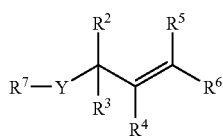

(3)

wherein $R^2$, $R^3$, $R^4$, $R^5$ and $R^6$ may be the same as or different from one another and each represent hydrogen atom or an organic group; $R^7$ represents an organic group; and Y represents oxygen atom or sulfur atom, the process including the step of reacting an allyl ester compound represented by following Formula (1):

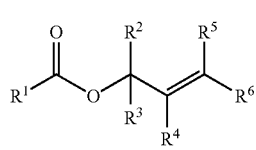

(1)

wherein $R^1$ represents hydrogen atom or an organic group; and $R^2$, $R^3$, $R^4$, $R^5$ and $R^6$ are as defined above, with a compound represented by following Formula (2):

$$R^7\text{—}Y\text{—}H \qquad (2)$$

wherein $R^7$ is an organic group; and Y is as defined above, in the presence of at least one transition element compound. Examples of the compound represented by Formula (2) include alcohols, phenols, thiol compounds, carboxylic acids and thiocarboxylic acids.

Examples of the transition element compound include iridium compounds and other compounds of elements of Group VIII of the Periodic Table of Elements.

The process of the present invention uses one or more transition element compounds as a catalyst and can thereby easily produce an allyl-containing compound under mild conditions. The process is highly versatile and can efficiently produce a wide variety of allyl-containing compounds.

The terms "allyl ester compound" and "allyl-containing compound" as used herein also include compounds except with one or more substituents replacing the hydrogen atom(s) of the allyl group (—$CH_2$—$CH$=$CH_2$). The term "transition element" means any of Group IIIA elements, Group IVA elements, Group VA elements, Group VIA elements, Group VIIA elements, Group VIII elements and Group IB elements of the Periodic Table of Elements. The term "organic group" herein is used in a broad meaning and includes not only carbon-atom-containing groups but also halogen atoms, nitro group, sulfo group, and other groups containing non-metallic atoms.

Further objects, features and advantages of the present invention will become apparent from the following description of the preferred embodiments.

DESCRIPTION OF THE PREFERRED EMBODIMENTS

According to the present invention, one or more transition element compounds (inclusive of elementary substances of transition elements) are used as a catalyst. Each of these transition element compounds can be used alone or in combination. Such transition elements include lanthanum, cerium and other Group IIIA elements (in particular, lanthanoid elements); titanium, zirconium and other Group IVA elements; vanadium and other Group VA elements; chromium, molybdenum, tungsten and other Group VIA elements; manganese and other Group VIIA elements; iron, cobalt, nickel, ruthenium, rhodium, palladium, osmium, iridium, platinum and other Group VIII elements; and copper, silver and other Group IB elements. Among them, Group VIII elements are preferred, of which platinum group elements including ruthenium, rhodium, palladium, osmium, iridium and platinum are more preferred, and iridium is specifically preferred.

Examples of the transition element compounds are elementary substances (metals), oxides, sulfides, hydroxides, halides (fluorides, chlorides, bromides and iodides), and sulfates of transition elements, oxoacids or salts thereof, inorganic complexes, and other inorganic compounds, each of which contains at least one transition element; cyanides, salts of organic acids (e.g., acetates), organic complexes, and other organic compounds of transition elements. Among them, organic complexes are preferred. Ligands constituting such complexes include known ligands. The transition elements in the transition element compounds each have a valency of from about 0 to about 6, and preferably from about 0 to about 3. In particular, iridium in the iridium compounds preferably has a valency of 1 or 3.

Examples of the transition element compounds include, by taking iridium compounds as an example, metal iridium, iridium oxide, iridium sulfide, iridium hydroxide, iridium fluoride, iridium chloride, iridium bromide, iridium iodide, iridium sulfate, iridic acid and salts thereof (e.g., potassium iridate), inorganic iridium complexes [e.g., hexaammineiridium(III) salts and chloropentaammineiridium(III) salts], and other inorganic compounds; iridium cyanide, organic iridium complexes, and other organic compounds. Such organic complexes include, but are not limited to, tris(acetylacetonato)iridium, dodecacarbonyltetrairidium(0), chlorotricarbonyliridium(I), di-μ-chlorotetrakis(cyclooctene)diiridium(I), di-μ-chlorotetrakis(ethylene)diiridium(I), di-μ-chlorobis(1,5-cyclooctadiene)diiridium(I), di-μ-chlorodichlorobis(pentamethylcyclopentadienyl)diiridium(III), trichlorotris(triethylphosphine)iridium(III), pentahydridobis(trimethylphosphine)iridium(V), chlorocarbonylbis(triphenylphosphine)iridium(I), chloroethylenebis(triphenylphosphine)iridium(I), (pentamethylcyclopentadienyl)dicarbonyliridium(I), bis{1,2-bis(diphenylphosphino)ethane}iridium(I) chloride, pentamethylcyclopentadienylbis(ethylene)iridium(I), carbonylmethylbis(triphenylphosphine)iridium(I), (1,5-cylooctadiene)(diphosphine)iridium(I) halides, 1,5-cyclooctadiene(1,2-bis(diphenylphosphino)ethane)iridium(I) haxafluorophosphate, (1,5-cyclooctadiene)bis(trialkylphosphine)iridium(I) halides, bis(1,5-cyclooctadiene)iridium tetrafluoroborate and (1,5-cyclooctadiene)(acetonitrile)iridium tetrafluoroborate.

Preferred iridium compounds include iridium complexes, of which organic iridium complexes are typically preferred. Among them, organic iridium complexes each having a specific ligand are especially preferred. Such specific ligands include, for example, cyclopentene, dicyclopentadiene, cyclooctene, 1,5-cyclooctadiene, ethylene, pentamethylcyclopentadiene, benzene, toluene, and other unsaturated hydrocarbons; acetonitrile and other nitrites; and tetrahydrofuran and other ethers. Examples of such preferred organic iridium complexes are di-μ-chlorotetrakis(cyclooctene)diiridium(I), di-μ-chlorotetrakis(ethylene)diiridium(I), di-μ-chlorobis(1,5-cyclooctadiene)diiridium(I), bis(1,5-cyclooctadiene)iridium tetrafluoroborate and (1,5-cyclooctadiene)(acetonitrile)iridium tetrafluoroborate. In the present invention, cationic iridium complexes such as bis(1,5-cyclooctadiene)iridium tetrafluoroborate and (1,5-cyclooctadiene)(acetonitrile)iridium tetrafluoroborate are specifically preferably used. Each of the iridium compounds can be used alone or in combination with each other and can be used in combination with the other transition element compounds.

The other transition element compounds than the iridium compounds include compounds corresponding to the iridium compounds, such as dichloro(1,5-cyclooctadiene)ruthenium, dichloro(1,5-cyclooctadiene)platinum and dichlorobis(1,5-cyclooctadiene)dirhodium. Among the other transition element compounds than the iridium compounds, preferred are organic complexes each containing a specific ligand such as cyclopentene, dicyclopentadiene, cyclooctene, 1,5-cyclooctadiene, ethylene, pentamethylcyclopentadiene, benzene, toluene and other unsaturated hydrocarbons; acetonitrile and other nitrites; and tetrahydrofuran and other ethers. Among them, cationic complexes are typically preferred.

The transition element compound can be used as intact or as being supported by a carrier (support). Such carriers include conventional carriers for supporting catalysts, such as silica, alumina, silica-alumina, zeolite, titania, magnesia and other metal oxides, as well as activated carbon. In a catalyst supported by a carrier, the amount of the transition element compound is, for example, from about 0.1% to 50% by weight, and preferably from about 1% to about 20% by weight relative to the weight of the carrier. The catalyst transition element compound can be supported by the carrier according to a conventional procedure such as impregnation, precipitation or ion exchange.

The amount of the transition element compound(s) is, for example, from about 0.0001 to about 1 mole, preferably from about 0.001 to about 0.3 mole, and more preferably from about 0.005 to about 0.1 mole per 1 mole of the compound represented by Formula (2) used as a reaction component.

Allyl Ester Compounds

In the allyl ester compounds represented by Formula (1), the substituents $R^1$, $R^2$, $R^3$, $R^4$, $R^5$ and $R^6$ independently represent hydrogen atom or an organic group. The organic group herein may be any organic group, as long as it does not adversely affect the reaction, such as an organic group that is not reactive under reaction conditions in the process of the present invention. Examples of such organic groups are halogen atoms, hydrocarbon groups, heterocyclic groups, substituted oxycarbonyl groups (e.g., alkoxycarbonyl groups, aryloxycarbonyl groups, aralkyloxycarbonyl groups and cycloalkyloxycarbonyl groups), carboxyl group, substituted or unsubstituted carbamoyl groups, cyano group, nitro group, sulfur acid groups, sulfur acid ester groups, acyl groups (e.g., acetyl group and other aliphatic acyl groups; and benzoyl group and other aromatic acyl groups), alkoxy groups (e.g., methoxy, ethoxy and other $C_1$–$C_6$ alkoxy groups), N,N-di-substituted amino groups (e.g., N,N-dimethylamino group and piperidino group), and groups each comprising two or more of these groups combined with each other. The carboxyl group and other groups may be protected by protecting groups which are known or conventionally used in the field of organic synthesis. The halogen atoms include fluorine, chlorine, bromine and iodine atoms. Among these organic groups, hydrocarbon groups and heterocyclic groups are preferred.

The hydrocarbon groups and heterocyclic groups also include hydrocarbon groups and heterocyclic groups each having one or more substituents. The hydrocarbon groups include aliphatic hydrocarbon groups, alicyclic hydrocarbon groups, aromatic hydrocarbon groups, and groups comprising these groups combined with each other. Examples of the aliphatic hydrocarbon groups are methyl, ethyl, propyl, isopropyl, butyl, isobutyl, s-butyl, t-butyl, pentyl, hexyl, decyl, dodecyl and other alkyl groups each having about 1 to about 20, preferably from about 1 to about 10, and more preferably from about 1 to about 3 carbon atoms; vinyl, allyl, 1-butenyl and other alkenyl groups each having about 2 to about 20, preferably from about 2 to about 10, and more preferably 2 or 3 carbon atoms; ethynyl, propynyl and other alkynyl groups each having about 2 to about 20, preferably from about 2 to about 10, and more preferably 2 or 3 carbon atoms.

Examples of the alicyclic hydrocarbon groups include cyclopropyl, cyclobutyl, cyclopentyl, cyclohexyl, cyclooctyl and other cycloalkyl groups each having about 3 to about 20, preferably from about 3 to 15, and more preferably from about 5 to about 8 members; cyclopentenyl, cyclohexenyl and other cycloalkenyl groups each having about 3 to about 20, preferably from about 3 to about 15, and more preferably from about 5 to about 8 members; perhydronaphthalen-1-yl group, norbornyl, adamantyl, tetracyclo[4.4.0.1$^{2,5}$.1$^{7,10}$] dodec-3-yl group and other bridged hydrocarbon groups. The aromatic hydrocarbon groups include, but are not limited to, phenyl, naphthyl and other aromatic hydrocarbon groups each having about 6 to about 14, and preferably from about 6 to about 10 carbon atoms.

Hydrocarbon groups each comprising an aliphatic hydrocarbon group and an alicyclic hydrocarbon group combined with each other include, for example, cyclopentylmethyl, cyclohexylmethyl, 2-cyclohexylethyl and other cycloalkyl-alkyl groups (e.g., $C_3$–$C_{20}$ cycloalkyl-$C_1$–$C_4$ alkyl groups). Hydrocarbon groups each comprising an aliphatic hydrocarbon group and an aromatic hydrocarbon group combined with each other include, for example, aralkyl groups such as $C_7$–$C_{18}$ aralkyl groups; and alkyl-substituted aryl groups such as phenyl or naphthyl group on which about one to about four $C_1$–$C_4$ alkyl groups are substituted.

Preferred hydrocarbon groups include $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{15}$ cycloalkyl-$C_1$–$C_4$ alkyl groups and $C_7$–$C_{14}$ aralkyl groups.

The hydrocarbon groups may each have one or more substituents. Examples of such substituents are halogen atoms, oxo group, hydroxyl group, substituted oxy groups (e.g., alkoxy groups, aryloxy groups, aralkyloxy groups and acyloxy groups), carboxyl group, substituted oxycarbonyl groups (e.g., alkoxycarbonyl groups, aryloxycarbonyl groups and aralkyloxycarbonyl groups), substituted or unsubstituted carbamoyl groups, cyano group, nitro group, substituted or unsubstituted amino groups, sulfo group and heterocyclic groups. The hydroxyl group and carboxyl group just mentioned above may be protected by a protecting group conventionally used in the field of organic synthesis. The alicyclic hydrocarbon groups and aromatic hydrocarbon groups may have aromatic or non-aromatic heterocyclic rings fused thereto.

Heterocyclic rings constituting the heterocyclic groups in $R^1$ and the other substituents include aromatic heterocyclic rings and non-aromatic heterocyclic rings. Such heterocyclic rings include, but are not limited to, heterocyclic rings each containing at least one oxygen atom as a hetero atom (e.g., furan, tetrahydrofuran, oxazole, isoxazole, γ-butyrolactone and other 5-membered rings; 4-oxo-4H-pyran, tetrahydropyran, morpholine and other 6-membered rings; benzofuran, isobenzofuran, 4-oxo-4H-chromene, chroman, isochroman, and other fused rings; 3-oxatricyclo[4.3.1.1$^{4,8}$]undecan-2-one ring, 3-oxatricyclo[4.2.1.0$^{4,8}$]nonan-2-one ring and other bridged rings); heterocyclic rings each containing at least one sulfur atom as a hetero atom (e.g., thiophene, thiazole, isothiazole, thiadiazole and other 5-membered rings; 4-oxo-4H-thiopyran and other 6-membered rings; benzothiophene and other fused rings); heterocyclic rings each containing at least one nitrogen atom as a hetero atom (e.g., pyrrole, pyrrolidine, pyrazole, imidazole, triazole and other 5-membered rings; pyridine, pyridazine, pyrimidine, pyrazine, piperidine, piperazine and other 6-membered rings; indole, indoline, quinoline, acridine, naphthyridine, quinazoline, purine and other fused rings). The heterocyclic groups may each have one or more substituents. Examples of such substituents are alkyl groups (e.g., methyl, ethyl, and other $C_1$–$C_4$ alkyl groups), cycloalkyl groups, aryl groups (e.g., phenyl and naphthyl groups), as well as the substituents which the hydrocarbon groups may have.

Preferred examples of $R^1$, $R^2$, $R^3$, $R^4$, $R^5$ and $R^6$ include hydrogen atom and hydrocarbon groups such as $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{12}$ cycloalkyl-$C_1$–$C_4$ alkyl groups and $C_7$–$C_{14}$ aralkyl groups. Among them, methyl group and other $C_1$–$C_3$ alkyl groups and phenyl group are typically preferred as $R^1$, and hydrogen atom, methyl group and other $C_1$–$C_3$ alkyl groups are typically preferred as $R^2$, $R^3$, $R^4$, $R^5$ and $R^6$.

Typical examples of the allyl ester compounds represented by Formula (1) are allyl acetate, 2-butenyl acetate, 1-methyl-2-butenyl acetate, 2-methyl-2-butenyl acetate, 1,2-dimethyl-2-butenyl acetate, allyl formate, allyl propionate and allyl benzoate, as well as linalyl acetate, d-citronellyl acetate, geranyl acetate, neryl acetate, phytyl acetate, lupeolyl acetate; geranyl formate, neryl formate, geranyl propionate, neryl propionate; geranyl benzoate, neryl benzoate and other terpenic allyl ester compounds.

An allyl ester compound formed in the reaction system can be used in the reaction. For example, an allyl ester formed in the reaction system by adding a corresponding allyl alcohol [$R^5R^6C$=$C(R^4)$—$C(R^2)(R^3)$—OH] and carboxylic acid [$R^1$—COOH] to the reaction system can be used as a raw material in the reaction. Typical examples of the allyl alcohol are allyl alcohol, 2-buten-1-ol, 1-methyl-2-buten-1-ol, 2-methyl-2-buten-1-ol, 1,2-dimethyl-2-buten-1-ol, as well as linalool, d-citronellol, geraniol and nerol. Typical examples of the carboxylic acid are formic acid, acetic acid, propionic acid and benzoic acid.

Compounds of Formula (2)

In the process of the present invention, the compound represented by Formula (2), i.e., any of a wide variety of hydroxyl compounds, thiol compounds, carboxylic acids, thiocarboxylic acids and other compounds can be used as a reaction component. In Formula (2), the organic group in $R^7$ can be any of organic groups as long as they do not adversely affect the reaction, such as organic groups that are not reactive under reaction conditions in the process. Examples of the organic groups are the organic groups exemplified in the substituents $R^1$, $R^2$, $R^3$, $R^4$, $R^5$ and $R^6$. Typical examples of the organic groups are hydrocarbon groups, heterocyclic groups and acyl groups. Examples of the hydrocarbon groups and heterocyclic groups are those exemplified in the substituents $R^1$, $R^2$, $R^3$, $R^4$, $R^5$ and $R^6$. The hydrocarbon groups and heterocyclic groups also include hydrocarbon groups and heterocyclic groups each having one or more substituents, as well as those each having a ring fused thereto. Such substituents are not specifically limited, as long as they do not adversely affect the reaction, and include the substituents which the hydrocarbon groups and heterocyclic groups in $R^1$, $R^2$, $R^3$, $R^4$, $R^5$ and $R^6$ may have. Examples of the acyl groups are groups represented by the formula: $R^8$—C(=O)—, wherein $R^8$ represents a hydrocarbon group or a heterocyclic group. Examples of the hydrocarbon group and the heterocyclic group in $R^8$ are the hydrocarbon groups and heterocyclic groups exemplified in $R^1$, $R^2$, $R^3$, $R^4$, $R^5$ and $R^6$.

The hydroxy compounds include, for example, primary alcohols, secondary alcohols, tertiary alcohols and phenols. The hydroxy compounds may each have plural hydroxyl groups and may be whichever of monohydric alcohols, dihydric alcohols, polyhydric alcohols, monohydric phenols, dihydric phenols and polyhydric phenols.

Typical examples of the primary alcohols are methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, glycerol, hexamethylene glycol, pentaerythritol and other saturated or unsaturated aliphatic primary alcohols each having about 1 to about 30, preferably from about 1 to about 20, and more preferably from about 1 to about 15 carbon atoms; cyclopentylmethyl alcohol, cyclohexylmethyl alcohol, 2-cyclohexylethyl alcohol and other saturated or unsaturated alicyclic primary alcohols; benzyl alcohol, 1,2- (1,3- or 1,4-)bis(hydroxymethyl)benzene, 1,2,3- (1,2,4- or 1,3,5-)tris(hydroxymethyl)benzene, 2-phenylethyl alcohol, 3-phenylpropyl alcohol, cinnamic alcohol and other aromatic primary alcohols; and 2-hydroxymethylpyridine and other heterocyclic primary alcohols. Primary alcohols each having one or more substituents on their hydrocarbon moiety include, but are not limited to, methyl glycolate, ethyl glycolate and other glycolic esters; ethylene glycol monomethyl ether, ethylene glycol monoethyl ether and other alkylene glycol monoalkyl ethers; ethylene glycol monoacetate and other alkylene glycol monoesters.

Typical examples of the secondary alcohols are 2-propanol, s-butyl alcohol, 2-pentanol, 3-pentanol, 3,3-dimethyl-2-butanol, 2-octanol, 4-decanol, 2-hexadecanol, 2-penten-4-ol, glycerol, 1,2-propanediol, 2,3-butanediol, 2,3-pentanediol, other vicinal diols, and other saturated or unsaturated aliphatic secondary alcohols each having about 3 to about 30, preferably from about 3 to about 20, and more preferably from about 3 to about 15 carbon atoms; 1-cyclopentylethanol, 1-cyclohexylethanol and other secondary alcohols each having an aliphatic hydrocarbon group and an alicyclic hydrocarbon group (e.g., a cycloalkyl group) combined with a carbon atom that is combined with a hydroxyl group; cyclobutanol, cyclopentanol, cyclohexanol, cyclooctanol, cyclododecanol, 2-cyclohepten-1-ol, 2-cyclohexen-1-ol, 2-adamantanol, 2-adamantanols each having an oxo group on their adamantane ring, 2-hydroxynorbornane, 2,5-dihydroxynorbornane, 3-hydroxytetracyclo[4.4.0.1$^{2,5}$.1$^{7,10}$]dodecane and other saturated or unsaturated alicyclic secondary alcohols (including bridged secondary alcohols) each having about 3 to about 20 members, preferably from about 3 to about 15 members, more preferably from about 5 to about 15 members, and typically from about 5 to about 8 members; 1-phenylethanol, 1-phenylpropanol, 1-phenylmethylethanol, diphenylmethanol and other aromatic secondary alcohols; and 1-(2-pyridyl)ethanol and other heterocyclic secondary alcohols.

Typical examples of the tertiary alcohols include t-butyl alcohol, t-amyl alcohol and other saturated or unsaturated aliphatic tertiary alcohols each having about 4 to about 30, preferably from about 4 to about 20, and more preferably from about 4 to about 15 carbon atoms; 1-cyclohexyl-1-methylethanol and other secondary alcohols each containing an aliphatic hydrocarbon group and an alicyclic hydrocarbon group (e.g., a cycloalkyl group and a bridged hydrocarbon group) combined with a carbon atom with which a hydroxyl group is combined; 1-methyl-1-cyclohexanol and other tertiary alcohols each containing a hydroxyl group and an aliphatic hydrocarbon group combined with one carbon atom constituting an alicyclic ring (e.g., a cycloalkane ring or a bridged carbon ring); 1-adamantanol, 1,3-adamantanediol and other bridged carbon ring-containing tertiary alcohols each containing a hydroxyl group at the bridgehead position of a bridged carbon ring; 1-phenyl-1-methylethanol and other aromatic tertiary alcohols; 1-methyl-1-(2-pyridyl)ethanol and other heterocyclic tertiary alcohols.

In addition to the above-exemplified alcohols, the alcohols also include glucose, fructose, sorbitol, isosorbide, amylose, cellulose, other chain or cyclic monosaccharides, disaccharides, polysaccharides, sugar alcohols and other saccharides having one or more hydroxyl groups; ethanolamine, diethanolamine, triethanolamine and other aminoalcohols; and alcohols each having one or more functional groups that are sensitive to a base, such as carboxylic ester group, nitro group or amido group.

Typical examples of the phenols include phenol, cresol, hydroquinone, resorcinol, catechol, 1-hydroxynaphthalene and other compounds each containing a hydroxyl group combined with an aromatic carbon ring; 2-hydroxypyridine, 3-hydroxypyridine, 4-hydroxypyridine, 3-hydroxyfuran, 3-hydroxythiophene and other compounds each containing a hydroxyl group combined with an aromatic heterocyclic ring. These hydroxy compounds may each have one or more substituents within a range not adversely affecting the reaction.

In addition to the above-exemplified compounds, preferred hydroxy compounds also include linalool, d-citronellol, carveol, menthol, geraniol, nerol and other monoterpenes; phytol and other diterpenes; cholesterol, lupeol, other triterpenes, and other terpenic alcohols.

The thiol compounds include aliphatic thiols, alicyclic thiols and aromatic thiols (thiophenols). These thiol compounds may each have plural mercapto groups.

Examples of the thiol compounds are compounds corresponding to the above-exemplified hydroxy compounds except with sulfur atom replacing the oxygen atom of their hydroxyl group. Typical examples of the aliphatic thiols are methanethiol, ethanethiol, 2-propanethiol, t-butanethiol, 1-mercapto-2-butene, 1-pentanethiol, 1-hexanethiol, 1-octanethiol and other saturated or unsaturated aliphatic thiols each having about 1 to about 30 carbon atoms, of which those having 1 to 20 carbon atoms are preferred, and those having 1 to 15 carbon atoms are more preferred. Examples of the alicyclic thiols are cyclopentylmethanethiol, cyclohexylmethanethiol, cyclohexanethiol and other saturated or unsaturated alicyclic thiols. These aliphatic thiols and alicyclic thiols may each have one or more substituents within a range not adversely affecting the reaction. Taking aliphatic thiols as an example, such substituted thiols include, for example, benzylthiol, 1-phenylethanethiol and other aromatic-ring-substituted aliphatic thiols; and 2-mercaptomethylpyridine, other heterocyclic-ring-substituted aliphatic thiols, and other substituted aliphatic thiols.

Typical examples of the aromatic thiols are thiophenol, thiocresol, mercaptoquinone, 1-thionaphthol and other compounds having mercapto group bonded to their aromatic carbon ring; 2-mercaptopyridine, 3-mercaptopyridine, 3-mercaptofuran, 3-mercaptothiophene and other compounds having mercapto group bonded to their aromatic heterocyclic ring. These aromatic thiols may each have one or more substituents within a range not adversely affecting the reaction.

In addition to the above-exemplified compounds, the thiol compounds also include compounds corresponding to the above-exemplified terpenic alcohols as preferred alcohol compounds, except with sulfur atom replacing the oxygen atom of their hydroxyl group.

The carboxylic acids include, for example, aliphatic carboxylic acids, alicyclic carboxylic acids and aromatic carboxylic acids. The carboxylic acids may each have plural carboxyl groups and may be whichever of monocarboxylic acids, dicarboxylic acids and polycarboxylic acids.

Typical examples of the aliphatic carboxylic acids are acetic acid, propionic acid, butyric acid, acrylic acid, methacrylic acid, stearic acid, behenic acid, palmitic acid and other monocarboxylic acids; and malonic acid, succinic acid, glutaric acid, adipic acid and other dicarboxylic acids. Typical examples of the alicyclic carboxylic acids are cyclopropanecarboxylic acid, cyclohexanecarboxylic acid and other monocarboxylic acids; and 1,1-cyclopropanedicarboxylic acid and other dicarboxylic acids. Typical examples of the aromatic carboxylic acids are benzoic acid, salicylic acid and other monocarboxylic acids; phthalic acid and other dicarboxylic acids.

In addition to the above-exemplified compounds, preferred examples of the carboxylic acids also include terpenic carboxylic acids including fencholic acid, camphanic acid, campholic acid, fusidic acid and other monocarboxylic acids; and cineolic acid, camphoric acid and other dicarboxylic acids.

Examples of the thiocarboxylic acids are aliphatic thiocarboxylic acids, alicyclic thiocarboxylic acids and aromatic thiocarboxylic acids. These thiocarboxylic acids may each have plural thiocarboxyl groups.

Examples of the thiocarboxylic acids are compounds corresponding to the above-exemplified compounds as the carboxylic acids, except with sulfur atom replacing the oxygen atom of their carboxyl group. Typical examples of the thiocarboxylic acids are thioacetic acid, thiopropionic acid, thiomethacrylic acid, thiomalonic acid and other aliphatic thiocarboxylic acids; cyclopropanethiocarboxylic acid, 1,1-cyclopropanedithiocarboxylic acid and other alicyclic thiocarboxlyic acids; and thiobenzoic acid, thiophthalic acid and other aromatic thiocarboxylic acids.

In addition to the above-exemplified compounds, preferred examples of the thiocarboxylic acids include compounds corresponding to the terpenic carboxylic acids exemplified as preferred carboxylic acids, except with sulfur atom replacing the oxygen atom of their carboxyl group.

Reaction

The reaction between the allyl ester compound represented by Formula (1) and the compound represented by Formula (2) is performed in the presence of, or in the absence of, a solvent. Examples of the solvent are hexane, heptane, octane and other aliphatic hydrocarbons; cyclohexane and other alicyclic hydrocarbons; benzene, toluene, xylene, ethylbenzene and other aromatic hydrocarbons; chloroform, dichloromethane, 1,2-dichloroethane and other halogenated hydrocarbons; diethyl ether, dimethoxyethane, tetrahydrofuran, dioxane and other ethers; acetone, methyl ethyl ketone and other ketones; methyl acetate, ethyl acetate, isopropyl acetate, butyl acetate and other esters; N,N-dimethylformamide, N,N-dimethylacetamide and other amides; acetonitrile, propionitrile, benzonitrile and other nitrites. Each of these solvents can be used alone or in combination.

The amount of the allyl ester compound represented by Formula (1) is, for example, from about 0.8 to about 15 equivalents, preferably from about 1 to about 12 equivalents, and more preferably from about 3 to about 10 equivalents per 1 equivalent of the compound represented by Formula (2). It is also acceptable that the allyl ester compound represented by Formula (1) is used in large excess.

From the viewpoint of yield of the target compound, the amount of a base in the reaction system in the process is preferably as small as possible and is, for example, preferably less than 0.001 mole, and more preferably 0.0001 mole or less per 1 mole of the compound represented by Formula (2). The reaction is generally performed in the absence of such a base. Examples of the base are sodium hydroxide, sodium carbonate and other inorganic bases; sodium acetate, sodium ethoxide and other organic bases.

When an allyl ester compound as a raw material is formed in the reaction system by adding the allyl alcohol and the carboxylic acid to the reaction system, the amount of the carboxylic acid is not specifically limited and is, for example from about 0.01 to about 2 moles and preferably from about 0.05 to about 1 mole per 1 mole of the allyl alcohol. The use of the carboxylic acid in a catalytic amount also enables the reaction to proceed. This reaction can be performed in the presence of a dehydrating agent such as a molecular sieve and/or may be performed while distilling off by-produced water. Where necessary, a strong acid such as sulfuric acid or p-toluenesulfonic acid can be used as a catalyst.

The reaction in the process may be performed in the presence of a polymerization inhibitor. A reaction temperature can appropriately be set depending on the types of the reaction components and the catalyst and is, for example, from about 20° C. to about 200° C., preferably from about 50° C. to about 150° C., and more preferably from about 70° C. to about 120° C. The reaction can be performed at normal atmospheric pressure (ambient pressure), under a reduced pressure or under a pressure (under a load). The atmosphere of the reaction is not specifically limited, as long as it does not adversely affect the reaction, and can be, for example, air atmosphere, nitrogen atmosphere or argon atmosphere. The reaction can be performed in any system such as batch system, semi-batch system and continuous system.

According to the process of the present invention, a corresponding allyl-containing compound represented by Formula (3) is formed under mild conditions as a result of the reaction. More specifically, the following embodiments [A], [B], [C] and [D] can be exemplified: [A] the use of a hydroxy compound as the compound of Formula (2) yields an allyl ester compound represented by Formula (3); [B] the use of a thiol compound as the compound of Formula (2) yields an allyl thioether compound of Formula (3); [C] the use of a carboxylic acid as the compound of Formula (2) yields an esterified allyl ester compound of Formula (3); and [D] the use of a thiocarboxylic acid as the compound of Formula (2) yields an esterified allyl thioester compound of Formula (3). After the completion of the reaction, reaction products can be separated and purified, for example, by separation means such as filtration, concentration, distillation, extraction, crystallization, recrystallization or column chromatography, or any combination of these separation means.

The present invention will be illustrated in further detail with reference to several examples below, which are not intended to limit the scope of the invention.

EXAMPLE 1

A mixture of bis(1,5-cyclooctadiene)iridium tetrafluoroborate [Ir(cod)$_2$]$^+$BF$_4^-$ (0.01 mmol) and toluene (1.0 ml) was treated with 1-octanol (130 mg, 1 mmol) and allyl acetate (5 mmol) at 100° C. for 5 hours with stirring. The reaction mixture was analyzed by gas chromatography to find that 1-octyl allyl ether, octyl acetate and octyl aldehyde were formed in yields of 90%, 2% and 2%, respectively, and octyl octanoate was formed in a trace amount with a conversion from 1-octanol of 95%.

EXAMPLE 2

A reaction was performed by the procedure of Example 1, except for using allyl acetate in an amount of 2 mmol. The reaction mixture was analyzed by gas chromatography to find that 1-octyl allyl ether, octyl acetate, octyl aldehyde and octyl octanoate were formed in yields of 56%, 1%, 1% and 11%, respectively, with a conversion from 1-octanol of 87%.

EXAMPLE 3

A reaction was performed by the procedure of Example 1, except for using geraniol instead of 1-octanol. The reaction mixture was analyzed by gas chromatography to find that 1-allyloxy-3,7-dimethyl-octa-2,6-diene and geranyl acetate were formed in yields of 85% and 1%, respectively.

EXAMPLE 4

A reaction was performed by the procedure of Example 1, except for using 1,4-butanediol instead of 1-octanol and using allyl acetate in an amount of 10 mmol. The reaction mixture was analyzed by gas chromatography to find that 3-(4-allyloxy-butoxy)-propene and 4-allyloxy-1-butanol were formed in yields of 78% and 6%, respectively.

EXAMPLE 5

A reaction was performed by the procedure of Example 1, except for using 1-adamantanol instead of 1-octanol. The reaction mixture was analyzed by gas chromatography to find that 1-adamantyl allyl ether was formed in a yield of 81%.

EXAMPLE 6

A reaction was performed by the procedure of Example 1, except for using 2-octanol instead of 1-octanol. The reaction mixture was analyzed by gas chromatography to find that 2-octyl allyl ether was formed in a yield of 69%.

EXAMPLE 7

A reaction was performed by the procedure of Example 1, except for using allyl alcohol (5 mmol), acetic acid (1 mmol) and toluene (1 mmol) instead of allyl acetate. The reaction mixture was analyzed by gas chromatography to find that 1-octyl allyl ether, octyl acetate and octylaldehyde were formed in yields of 41%, 2% and 6%, respectively.

EXAMPLE 8

A reaction was performed by the procedure of Example 1, except for using allyl alcohol (5 mmol) and acetic acid (1 mmol) instead of allyl acetate and further using molecular sieve 3A (100 mg) and toluene (1 ml). The reaction mixture was analyzed by gas chromatography to find that 1-octyl allyl ether, octyl acetate and octylaldehyde were formed in yields of 53%, 2% and 13%, respectively.

EXAMPLE 9

A mixture of bis(1,5-cyclooctadiene)iridium tetrafluoroborate $[Ir(cod)_2]^+BF_4^-$ (0.01 mmol) and toluene (1.0 ml) was treated with phenol (1 mmol) and allyl acetate (5 mmol) with stirring at 100° C. The reaction mixtures after 5 hours and after 15 hours of the reaction were analyzed by gas chromatography. In the reaction mixture after 5 hours, phenyl allyl ether was formed in a yield of 21% with a conversion from phenol of 23%. In the reaction mixture after 15 hours, phenyl allyl ether was formed in a yield of 51% with a conversion from phenol of 51%.

EXAMPLE 10

A reaction was performed by the procedure of Example 9, except for using benzyl alcohol (1 mmol) instead of phenol. The reaction mixtures after 5 hours and 15 hours of the reaction were analyzed by gas chromatography, respectively. In the reaction mixture after 5 hours, benzyl allyl ether, benzyl acetate and benzaldehyde were formed in yields of 71%, 2% and 2%, respectively, with a conversion from benzyl alcohol of 83%. In the reaction mixture after 15 hours, benzyl allyl ether, benzyl acetate and benzaldehyde were formed in yields of 82%, 2% and 4%, respectively, with a conversion from benzyl alcohol of 99%.

EXAMPLE 11

A reaction was performed by the procedure of Example 9, except for using allyl alcohol (1 mmol) instead of phenol. The reaction mixtures after 5 hours and 15 hours of the reaction were analyzed by gas chromatography, respectively. In the reaction mixture after 5 hours, diallyl ether was formed in a yield of 56% with a conversion from allyl alcohol of 83%. In the reaction mixture after 15 hours, diallyl ether was formed in a yield of 61% with a conversion from allyl alcohol of 99%.

EXAMPLE 12

A reaction was performed by the procedure of Example 9, except for using benzoic acid (1 mmol) instead of phenol. The reaction mixture after 15 hours of the reaction was analyzed by gas chromatography to find that allyl benzoate was formed in a yield of 6%.

EXAMPLE 13

A reaction was performed by the procedure of Example 9, except for using hexanethiol (1 mmol) instead of phenol. The reaction mixture after 5 hours was analyzed by gas chromatography to find that hexyl allyl thioether was formed in a yield of 23%.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing an allyl-containing compound represented by following Formula (3):

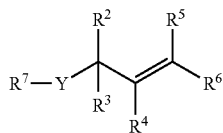
(3)

wherein $R^2$, $R^3$, $R^4$, $R^5$ and $R^6$ may be the same as or different from one another and each represent hydrogen atom or an organic group; $R^7$ represents an organic group; and Y represents oxygen atom or sulfur atom, the process comprising the step of reacting an allyl ester compound represented by following Formula (1):

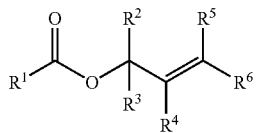
(1)

wherein $R^1$ represents hydrogen atom or an organic group; and $R^2$, $R^3$, $R^4$, $R^5$ and $R^6$ are as defined above, with a compound represented by following Formula (2)

$$R^7—Y—H \qquad (2)$$

wherein $R^7$ is an organic group; and Y is as defined above, wherein the compound represented by Formula (2) is one selected from the group consisting of alcohols and thiol compounds, provided that the compound represented by Formula (2) is not a phenol,
in the presence of a catalytic amount of an iridium compound.

2. The process according to claim 1, wherein said iridium compound is an organic iridium complex.

3. The process of claim 2, wherein said organic iridium complex is a cationic iridium complex.

4. The process of claim 2, wherein said organic iridium complex is selected from the group consisting of
di-µ-chlorotetrakis(cyclooctene)diiridium(I), di-µ-chlorotetrakis(ethlyene)diiridium(I),
di-µ-chlorobis(1,5-cyclooctadiene)diiridium(I),
bis(1,5-cyclooctadiene)iridium tetrafluoroborate, and
(1,5-cyclooctadiene)(acetonitrile)iridium tetrafluoroborate.

5. The process of claim 1, wherein the amount of a base in the reaction system in the process is less than 0.001 mole per 1 mole of the compound represented by Formula (2).

* * * * *